United States Patent [19]
Gassler et al.

[11] Patent Number: 5,339,154
[45] Date of Patent: Aug. 16, 1994

[54] METHOD AND APPARATUS FOR OPTICAL MEASUREMENT OF OBJECTS

[75] Inventors: Joachim Gassler, Geisingen; Robert Massen, Radolfszell, both of Fed. Rep. of Germany

[73] Assignee: Kaltenbach & Voigt Gmb & Co., Biberach/Riss, Fed. Rep. of Germany

[21] Appl. No.: 969,923

[22] Filed: Oct. 15, 1992

[30] Foreign Application Priority Data

Oct. 15, 1991 [DE] Fed. Rep. of Germany ....... 4134117

[51] Int. Cl.$^5$ .............................................. G01B 11/24
[52] U.S. Cl. .................................................... 356/376
[58] Field of Search ................... 356/376; 250/237 G; 364/560

[56] References Cited

U.S. PATENT DOCUMENTS

| | | | |
|---|---|---|---|
| 4,648,717 | 3/1987 | Ross et al. ............................. | 356/376 |
| 4,668,094 | 5/1987 | Matsumoto et al. .................. | 356/376 |
| 4,802,759 | 2/1989 | Matsumoto et al. .................. | 356/376 |
| 5,175,601 | 12/1992 | Fitts ...................................... | 356/376 |

*Primary Examiner*—F. L. Evans
*Attorney, Agent, or Firm*—Scully, Scott, Murphy & Presser

[57] ABSTRACT

The invention relates to a method for optical measurement of objects, in particular teeth, with a projector, with beam path diverging from a projector central point, imaging on the object a pattern of different ranges of brightness, which pattern is imaged on the sensor surface of a camera, arranged in a certain disposition in space at a parallax angle to the projector, with a beam path converging in the direction of a camera central point, and is split up into image points, the light intensities of which are measured and stored, and from the light intensities of the image points the phase position of the latter is determined and stored. For the purpose of error-free measurement it is proposed that the position in space of the projector central point, of the camera central point and also of sensor elements of the sensor surface be calculated and stored, the pattern in the plane of projection be split up into image points, the position in space of the latter be calculated and stored, image points of equal phase position be correlated with each other and the position in space of straight lines through image points of equal phase position and the projector and camera central point and also the space coordinates of the points of intersection of these straight lines be calculated. The storage, correlation and calculation occur in a computer.

7 Claims, 4 Drawing Sheets

METHOD AND APPARATUS FOR OPTICAL MEASUREMENT OF OBJECTS

TECHNICAL FIELD OF THE INVENTION

The invention relates to a method for optical measurement of objects, in particular artificial or natural teeth in or outside the patient's mouth, and also an apparatus for carrying out the method.

BACKGROUND OF THE INVENTION AND PRIOR ART

Such a method and the corresponding apparatus having a measuring probe containing the projector and the camera are known from U.S. Pat. No. 4,952,149 and are described there with the aid of an exemplary embodiment on the basis of the projection of the pattern by means of parallel light beams (telecentric projection). Mentioned briefly, moreover, as an alternative, is the projection with the aid of diverging light beams (central projection).

Both the telecentric and the central projection are represented here in FIGS. 1 and 2.

As FIG. 1 shows, in the case of this known method a stripe pattern $M_P$ located in the plane of projection PE of the projector and with sinusoidal brightness distribution transverse to the stripe direction is projected by means of the parallel light beams L at the angle of incidence $\alpha$ onto the object to be measured, represented by the object plane OE, and also onto a reference plane RE and the respective images $M_{OE}$ and $M_{RE}$ are taken up by the camera, that is, imaged on the sensor surface SF thereof. The difference between the phase positions determined from the two takes for each camera-side image point $BP_K$ or the path difference $\Delta x$ between the sinusoidal waves of the two patterns $M_{OE}$ and $M_{RE}$ is, in accordance with the equation $tg\alpha = \Delta x/\Delta z$, a direct measure of the distance $\Delta z$ between the reference plane RE and the object-side image point $BP_O$ imaged on the object or on the corresponding object surface point. Since the angle of incidence $\alpha$ is the same for all projected light beams, the range of validity of this equation extends to all object surface points encountered by the projected light bees.

In view of the telecentric projection, the projector used requires an optical system, the diameter of which is at least equal to the diagonals of the surface on the object to be illuminated. The result of this, for the measurement of teeth in the patient's mouth, is undesirably large dimensions and, consequently, insufficient ease of handling of the measuring probe.

In contrast therewith, the measuring probe or the projector with the optical system formed for the central projection is of considerably smaller dimensions and is thus better suited for the measurement of teeth in the patient's mouth. The diverging beam course of this optical system is disadvantageous though in so far as it excludes the use of the above-mentioned relationship between phase difference and the distance $\Delta z$. The stripe pattern $M_{RE}$ or $M_{OE}$ respectively projected onto the reference plane RE or the object plane OE is namely distorted, as shown in FIG. 2, in comparison with the stripe pattern $M_{PE}$ located in the plane of projection PE in accordance with the different angles of incidence $\alpha,\beta$ of the individual light beams L. In other words, the camera no longer observes a displacement of the reference plane by $\Delta z$, as in the case of telecentric projection, as the sole displacement of the phase position of the stripe pattern, but as a mixture of phase displacement and different change of the wavelength. Thus the distance values $\Delta z$ determined, in the same way as the contour image of the object derived from them, contain different error contents corresponding to the different distortions of the wavelength.

OBJECT OF THE INVENTION

It is the object of the invention to develop further a method and an apparatus of the kind mentioned in the introduction so that the contour image of the object can be determined in an error-free manner.

SUMMARY OF THE INVENTION

According to the present invention there is provided a method for optical measurement of objects, in particular artificial or natural teeth in or outside the patient's mouth, having the following steps:

a) by means of at least one projector, and with a beam path which diverges from a projector central point, at least one pattern, arranged in the plane of the projection and with at least two ranges of different brightness, is imaged on the object to be measured;

b) the pattern imaged on the object is imaged on the sensor surface of at least one camera, which is associated in a certain disposition in space with the projector and which is directed at the object at a parallax angle in relation to said projector, with a beam path converging in the direction of a camera central point and is split up by sensor elements of the sensor surface into individual camera-side image points, the light intensities of which are measured and stored in a computer;

c) by means of the computer, the phase position of each camera-side image point is determined from its light intensity and stored in the computer, which phase position corresponds to the phase position of the respectively associated object-side image point, imaged on the object, and is dependent upon the vertical position thereof, wherein d) the disposition in space, relative to a reference system of coordinates, of the projector central point and of the camera central point and also of the sensor elements of the sensor surface is determined and stored in the computer, e) the pattern in the plane of projection of the projector is split up into projector-side image points and the respective positions in space of these image points, relative to the reference system of coordinates, are determined and stored in the computer, f) by means of the computer camera-side image points and projector-side image points of equal phase position are correlated with each other, and g) the computer determines the disposition in space, relative to the reference system of coordinates, of imaginary projector-side and camera-side straight lines going through the correlated projector-side or camera-side image points of equal phase position and the projector central point or the camera central point respectively, and also determines the space coordinates of the points of intersection of these straight lines and thus the disposition in space of the respectively correlated object-side image points or object surface points.

The diverging beam course of the central projection, which in the case of the previous method for determining the vertical position of the individual object surface points or their distance from the reference plane resulted in errors, is the basis for the method according to the invention and is used in this method for error-free determination of the vertical position of the object surface points. The method according to the invention is distinguished by low outlay in terms of time and computing; for example, the take, required in the prior art, of the reference phase image which shows the phase position of the pattern, projected onto the reference plane, on the sensor surface of the camera is dispensed with; the positions of the individual object surface points are specified directly according to the invention by their space coordinates so that the conversion required in the prior art of the distance $\Delta z$ to the vertical or Z coordinate and the combination thereof with the separately determined x-, y-coordinates is dispensed with.

According to the present invention there is also provided apparatus for carrying out the method of the invention, wherein the projector has, in the plane of projection, an LCD unit which can be activated by means of an LCD matrix for the purpose of producing different patterns and also a light source and an optical system, the diverging light beams of which radiate through the LCD unit for the purpose of imaging the patterns on the object to be measured, the camera is a CCD camera with a CCD unit, the CCD matrix of which splits up the pattern taken up into individual camera-side (matrix) image points, the computer delivers to the LCD unit for each projector-side (matrix) image point a brightness signal which corresponds to the pattern to be produced, the CCD camera delivers to the computer for each camera-side (matrix) image point an evaluation signal which corresponds to the latter's measured brightness, and the computer effects the coordination of the image points of the LCD matrix and the CCD matrix and also the calculation of the space coordinates of the image points on the object side or the object surface points respectively.

With regard to the apparatus according to the invention, the central projection permits the use of measuring probes of the smallest structural size in, for example, the form of miniature endoscopes which are connected to the computer and in which camera and projector are installed.

In order to avoid ambiguities in the correlation of the camera-side and projector-side image points of equal phase position, a pattern can be imaged on the object, which pattern has a brightness distribution from the evaluation of which result different phase positions, which in each case occur only once, for the projector-side and the camera-side image points. In this way, as a result, the camera-side and thus as well the projector-side image points each have different phase positions.

The demands in respect of the measuring accuracy of the sensor surface and the brightness contrast can be reduced without losses in terms of the accuracy of the determined phase positions, if a pattern with periodically repeating values of equal brightness, for example a stripe pattern with analog, preferably sinusoidal brightness distribution transverse to the stripe direction, is imaged on the object. With increasing number of stripes, the resolution and with that the measuring density and yet also the danger of ambiguities in the correlation of camera-side and projector-side image points increase. In this case it is favourable to image on the object and evaluate at least two stripe patterns, a first, rough stripe pattern with a comparatively small number of stripes and a second, fine stripe pattern with a comparatively large number of stripes, one after the other, whereby the ambiguities, which are a result of the higher resolution of the second stripe pattern, in the correlation of the projector-side and camera-side image points of equal phase position are eliminated by consideration of the projector-side and camera-side image points of equal phase position of the first stripe pattern.

When a stripe pattern is used, it is advantageous to split this up in the plane of projection into image point lines which extend in the stripe direction and to determine the position in space of imaginary planes laid through the image point lines and the projector central point and also the space coordinates of the points of intersection of those of these planes and those camera-side straight lines which go through image point lines or camera-side image points of equal phase position.

According to a further development of the invention the stripe pattern is imaged on the object at least three times with, in each case, phase position shifted by the same phase angle transversely to the stripe direction, and is evaluated according to the known phase shift method for the exact determination of the phase position of the camera-side image points.

BRIEF DESCRIPTION OF THE DRAWINGS

The invention is described in the following with the aid of preferred exemplary embodiments with reference to FIGS. 3 to 6 of the drawings.

In the drawings.

DETAILED DESCRIPTION OF PREFERRED EMBODIMENTS ACCORDING TO THE INVENTION

Figure 1:
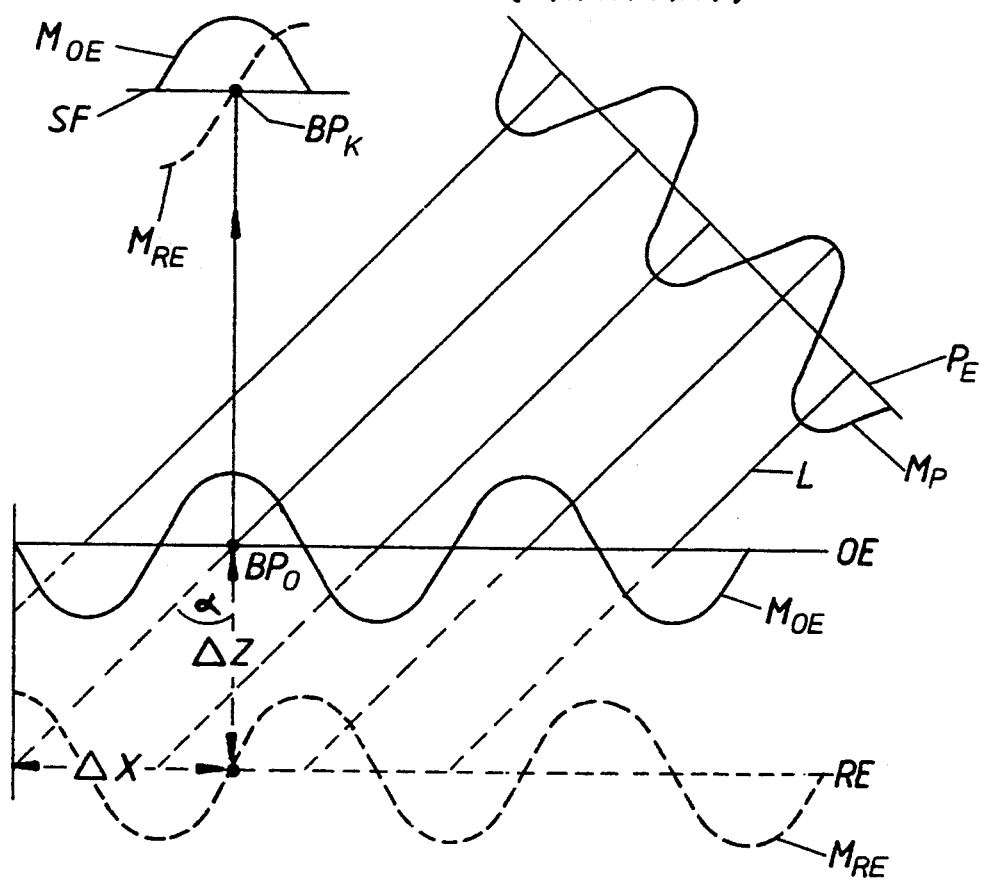
FIGS. 1 and 2 show schematic representations of the optical measuring method known from the prior art with telecentric and with central projection.
Figure 2:
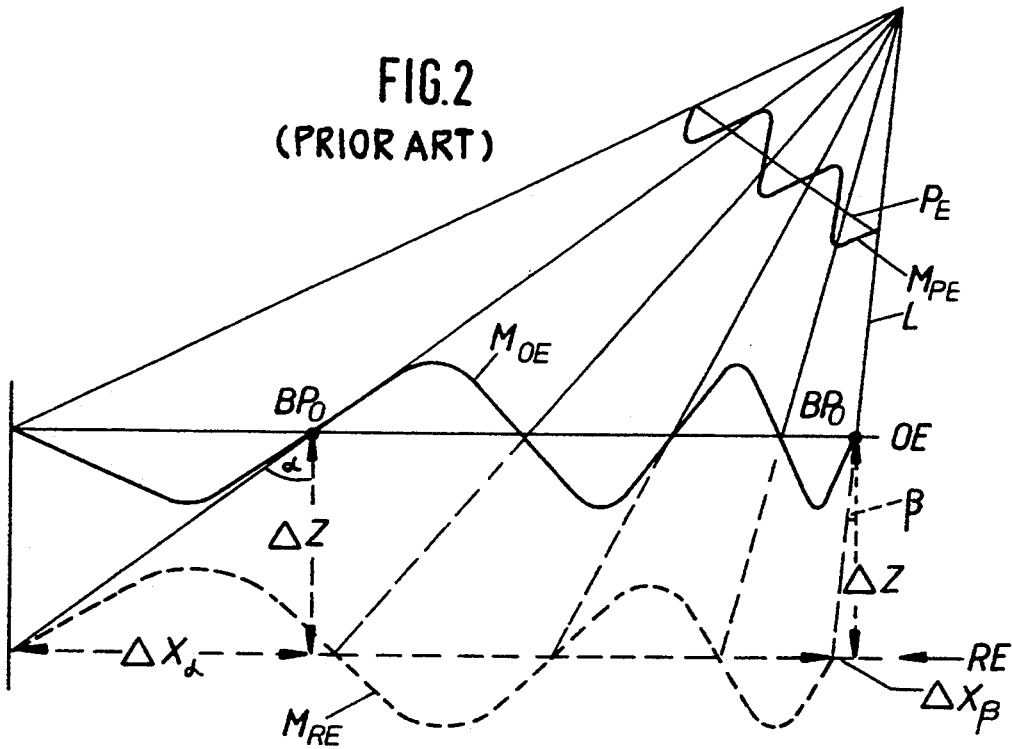
Figure 3:
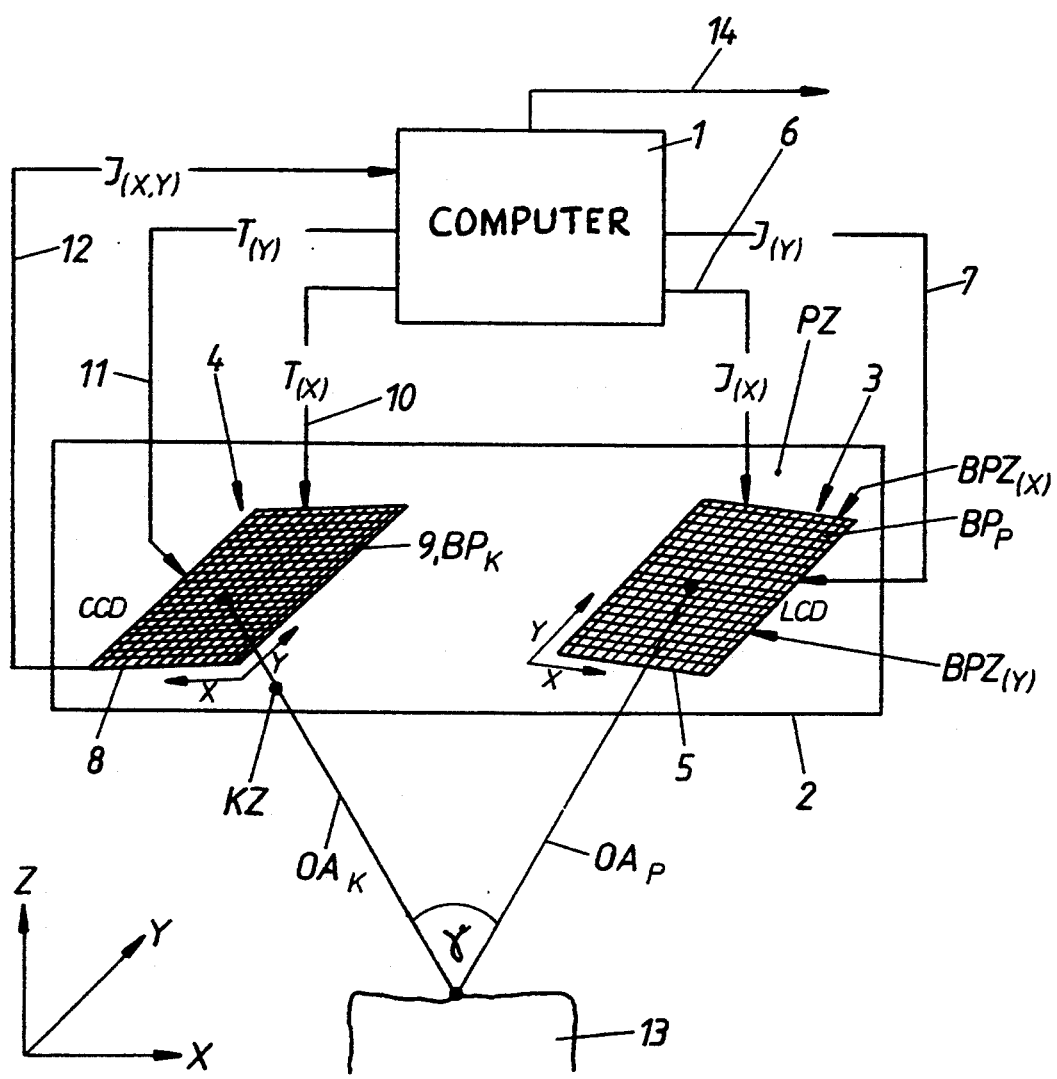
FIG. 3 shows a schematic representation of the preferred exemplary embodiment of the apparatus according to the invention.

The apparatus represented in FIG. 3 comprises a computer 1 and a measuring probe 2 in which a projector 3 and a camera 4 are arranged. The projector 3 is formed for central projection and is of conventional construction with a light source which is not shown, an optical system which is likewise not shown and comprises a concave mirror, a condenser and a projection lens, and with an LCD unit 5 which is arranged in a plane of projection between the condenser and the projection lens and is illuminated by transmitted light. The concave mirror collects the light radiated from the light source and images the light source in itself. The condenser covers a large space angle of the radiation and images the light source in the projection lens, the focal point of which here is designated as the projector central point PZ and from which the light beams issue in the form of a divergent bundle of rays. For the sake of simplicity in FIGS. 3 and 4 this projector central point PZ in the beam path is represented as being in front of the LCD unit 5. The latter comprises an LCD area matrix with image point lines $BPZ_{(x)}$, $BPZ_{(y)}$ extending in the X- and Y-direction consisting of projector-side (matrix) image points $BP_P$ which can be activated by the computer 1 by actuation with brightness signals $I_{(x)}$, $I_{(y)}$ by way of control lines 6 and 7 for the generation of different patterns. The data for these patterns is stored in the computer 1.

The camera 4 is a conventional CCD camera with an optical system which is not shown and a CCD unit 8 which is arranged in an image plane as a sensor surface with a CCD area matrix, the photosensor elements 9 of which are arranged in the X- and Y-direction and which can be activated by application of clock pulses $T_{(x)}$, $T_{(y)}$ by way of control lines 10 and 11 from the computer 1. The electric pulses or evaluation signals $I_{(x)}$, $I_{(y)}$ which are sequentially available at the output of the CCD unit 8 and which are proportional to the intensity I of the luminous radiation which impinges upon it are directed by way of a signal line 12 to the computer 1. As the camera optical system images an object 13 to be measured, for example a tooth, in a reversed manner on the CCD unit 8 and thus the beam path diverges from the focal point of the lens system in both directions, the camera, for the sake of simplicity, is represented as a pin-hole camera which has the same beam path and in the entry opening of which lies the point of intersection of the light beams L designated as the camera central point KZ.

The projector central point PZ, the camera central point KZ and also the LCD unit 5 and the CCD unit 8 are arranged in a certain position in space within a reference system of coordinates which is determined upon the calibration of the projector 3 and the camera 4 preferably carried out with the aid of the so-called bundle compensation. The optical axes $OA_P$ and $OA_K$ of the projector 3 and of the camera 4 include a parallax angle $\gamma$.

The function of the apparatus according to the invention is described in the following with reference to the measurement of teeth in the mouth of a patient.

The measuring probe 2 is held over the tooth 13 to be measured and switched to "function" in order to set the measurement into operation with the following sequence. With the projector 3 four first and four second stripe patterns $M1_1$–$M1_4$ and $M2_1$–$M2_4$ (represented as M1 and M2 in FIG. 5) are imaged successively on the tooth 13. For this purpose, the computer 1 activates the LCD unit 5 of the projector 3 with control signals $I_{(x)}$, $I_{(y)}$ corresponding to the respective stripe pattern so that the respectively associated image points $BP_P$ of the LCD matrix are activated and form the respective stripe pattern (illustrated in FIG. 4 in a representative manner for $M1_1$–$M1_4$ and $M2_1$–$M2_4$ by $M_P$). The light beams L issuing from the projector central point PZ and modulated by the stripe pattern $M_P$ generated by the LCD unit 5 are projected onto the tooth 13 and there image the respective stripe pattern which is distorted in accordance with the topography of the tooth 13 or is phase-shifted in the individual object surface points PO in accordance with the vertical position thereof (z-coordinate).

Figure 5:
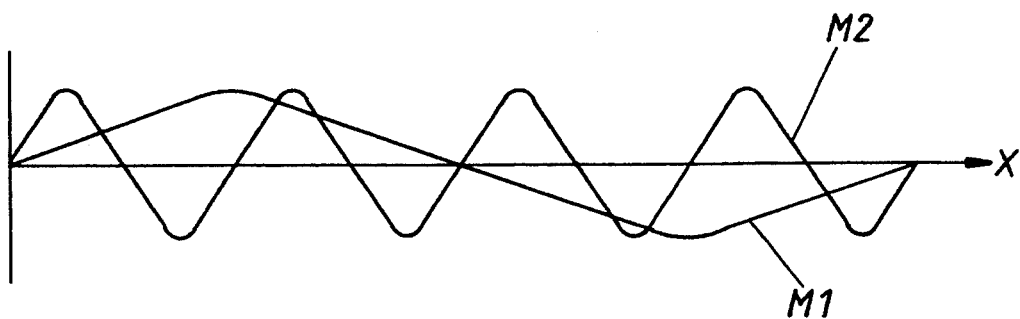
FIG. 5 shows a representation of the so-called hierarchical method with successive projection of several sinusoidal stripe patterns.
Figure 6:
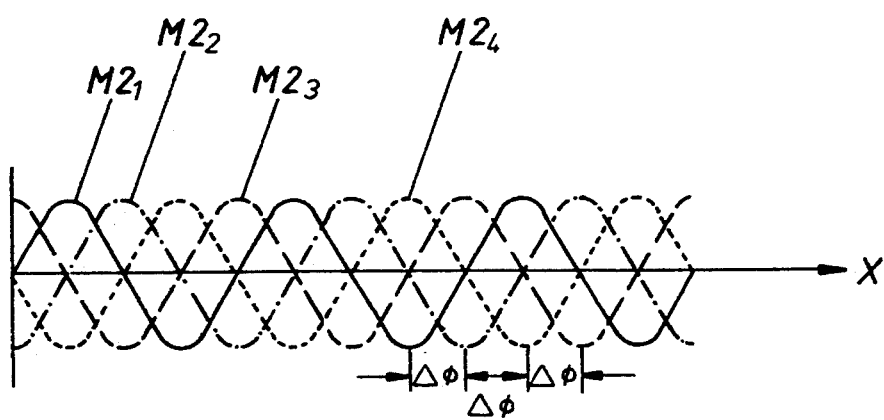
FIG. 6 shows a representation of the so-called phase shift method with successive projection of several sinusoidal stripe patterns.

All the stripe patterns $M1_1$–$M1_4$ and $M2_1$–$M2_4$ have an analog brightness distribution, sinusoidal in the X-direction of the LCD unit 5. As shown in FIG. 5, the wave number or repetency of the second stripe pattern $M2_1$–$M2_4$ (represented as M2) is 4 times greater than the wave number with the value 1 of the first stripe patterns $M1_1$–$M1_4$ (represented as M1). The second stripe patterns $M2_1$–$M2_4$ are, as shown in FIG. 6, identical, yet phase-shifted in relation to each other by, in each case, 90°. The same applies to the first stripe patterns $M1_1$–$M1_4$ (not represented).

Each of the stripe patterns $M1_1$–$M1_4$ and $M2_1$–$M2_4$ imaged on the tooth 13 is taken up by the camera 4, that is, imaged on its CCD unit 8, (it is denoted in FIG. 4 as $M_K$) and split up by means of the sensor elements 9 into individual camera-side image points $BP_K$. The computer 1 activates these sensor elements 9 by way of the control lines 10, 11, which sensor elements thereby generate electric pulses $I_{(x)}$·$I_{(y)}$ which correspond to the light intensity I of the image points $BP_K$ superimposed upon them in each case and which are directed sequentially by way of the signal line 12 to the computer 1 and there are evaluated according to the hierarchical phase shift method.

According to the formula $$I_{(x,y)} = I_m(x,y)[1 + K_{(x,y)} \cos(\phi_{(x,y)} + \Delta\phi)]$$

the light intensity $I_{(x,y)}$ measured for each camera-side image point $BP_K$ is a measure of the phase position $\phi$ of this image point, which for its part is a measure of the vertical position (z-coordinate) of the object surface point PO, onto which the relevant object-side image point $BP_O$ is imaged.

Although for the purpose of determining the three unknowns I, $I_m$ (=background brightness, that is, brightness of the object without pattern imaged thereon) and K (contrast of the pattern) only three equations, that is, the light intensity measurements of three respectively phase-shifted first and second stripe patterns $M1_1$–$M1_3$ or $M2_1$–$M2_3$, are required, in the present exemplary embodiment according to the so-called 4-phase-shift method in each case a fourth phase-shifted stripe pattern, namely $M1_4$ and $M2_4$, is incorporated into the measurement or evaluation, whereby the computing processes are considerably simplified for the determination of the phase position $\phi$.

From each of the two sequences of the first and second stripe patterns $M1_1$–$M1_4$ and $M2_1$–$M2_4$ taken up with the camera 4, the computer 1 determines for each camera-side image point $BP_K$ the phase position $\phi$ which is independent of the contrast and of the background brightness or for the totality of all the camera-side image points $BP_K$ the corresponding phase image according to the equation $$\phi_{(x,y)} = \arctan \frac{I_{270°(x,y)} - I_{90°(x,y)}}{I_{180°(x,y)} - I_{0°(x,y)}}$$

Regions of these phase images determined in this way, the background brightness and contrast of which lie outside a preset interval, are masked out by the computer 1, that is, the phase position of the relevant image points $BP_K$ is replaced by a corresponding code word and is thereby excluded from further evaluation. The brightness image $I_{m(x,y)}$ and the contrast image $K_{(x,y)}$ are required for this. Both are calculated directly from the four respectively phase-shifted first and second stripe patterns $M1_1$–$M1_4$ and $M2_1$–$M2_4$ as follows:

$$I_{m(x,y)} = 0.25 \times (I_{0°(x,y)} + I_{90°(x,y)} + I_{180°(x,y)} + I_{270°(x,y)})$$

$$K_{(x,y)} = \sqrt{(I_{90°(x,y)} - I_{0°(x,y)})^2 + (I_{180°(x,y)} - I_{270°(x,y)})^2}$$

This masking-out prevents all invalidity regions, such as, for example, edge regions, shadow zones, places which reflect to an excessively great extent and the like, from entering into the evaluation and from resulting in errors in the optical measurement.

Figure 4:
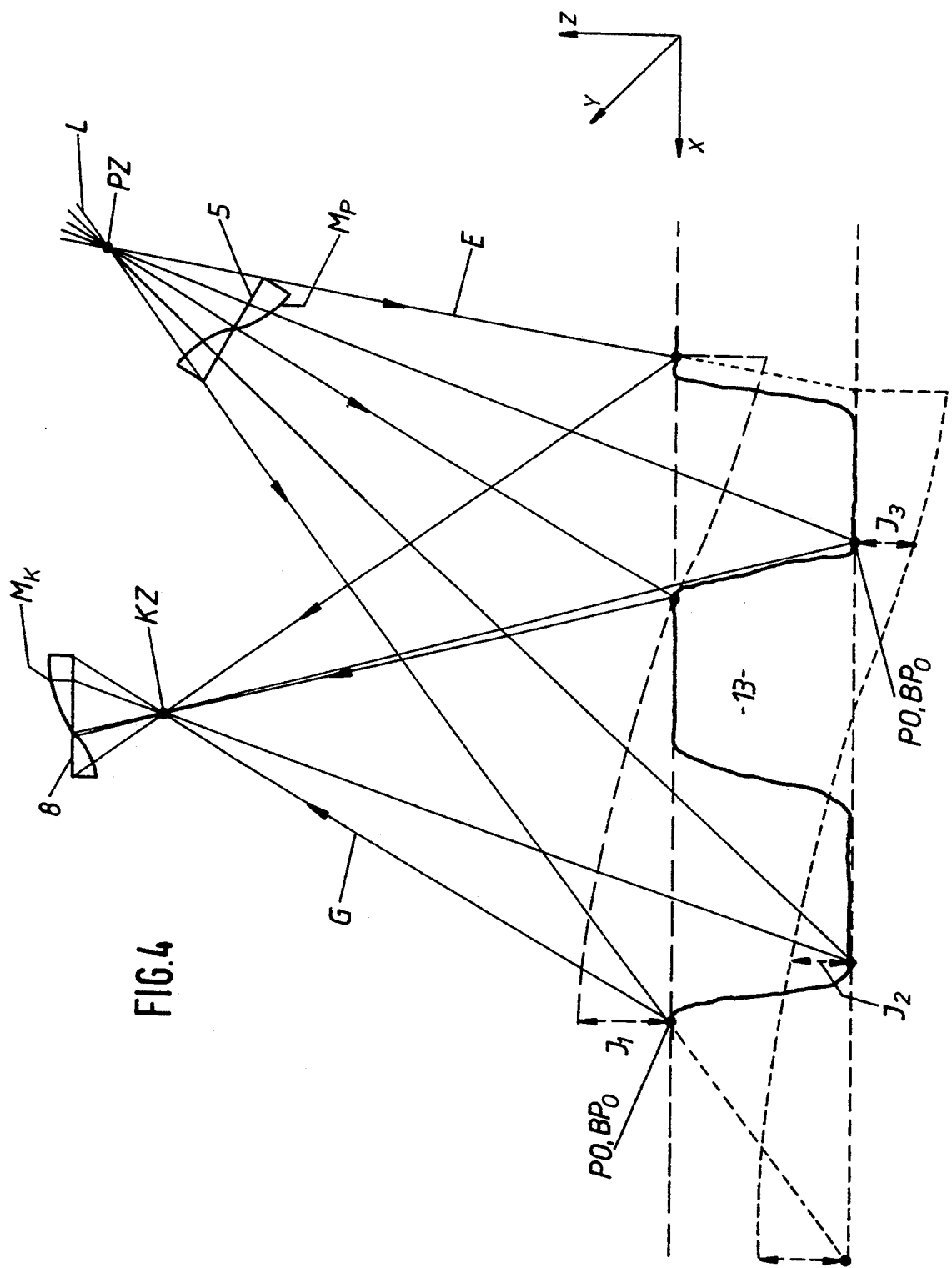
FIG. 4 shows a schematic representation of the method according to the invention.

The computer 1 calculates the position in space, relative to the reference system of coordinates, of imaginary straight lines G which go through the image points $BP_K$ and the camera central point KZ. Furthermore, the computer 1 determines the position in space, relative to the reference system of coordinates, of imaginary planes E going through the image point lines $BPZ_{(y)}$ of the LCD matrix and the projector central point PZ (represented by straight lines in FIG. 4) in order thereupon to determine for each of the two masked-out phase images from the straight line and plane equations the space coordinates x,y,z of the points of intersection of those planes E and those straight lines G which go through projector-side image point lines $BPZ_{(y)}$ or camera-side image points $BP_K$ of equal phase position. The calculations are based on known mathematical methods. The totality of the points of intersection determined from each phase image produces a respective topographic image of the measured tooth surface, as each point of intersection is identical with the object surface point PO upon which the light beam incident along the respectively associated plane E and reflected along the respectively coordinated straight line G impinges and images the respectively correlated projector-side image point $BP_K$ as an object-side image point $BP_O$. This state of affairs is represented in FIG. 4, though with regard to the stripe pattern $M_P$ which has a sinusoidal brightness distribution with brightness values which are different in each case and which merely occur once. In other words, the sinusoidal wave representing the stripe pattern extends over an angular range of 180°, that is, from the point of maximum positive deviation to the point of maximum negative deviation. In the case of such a stripe pattern the planes E and the straight lines G characterise projector-side image point lines $BPZ_{(y)}$ or camera-side image points $BP_K$ of, in each case, differing phase position so that no ambiguities occur in the correlation of the straight lines G and the planes E, that is, straight lines and planes can be correlated with each other in each case in pairs in order to determine their points of intersection, In addition, in the case of the evaluation of the phase image determined from the sequence of the first stripe patterns $M1_1$ to $M1_4$ with correspondingly adjusted small wave number of these stripe patterns, no ambiguities (phase jumps) occur with regard to the phase position of the projector-side and the camera-side image points, yet the resolution of the resultant topographic image is too small for the requirements set. In order to attain the required resolution, the sequence of the second stripe patterns $M2_1$–$M2_4$ is used with correspondingly high wave number, in the evaluation of which, in the manner previously described, however, ambiguities can occur in the correlation of the straight lines and the planes of, in each case, equal phase position. These ambiguities are eliminated by hierarchical development or linkage of both phase images, with the computer correlating the straight lines and planes, which can be correlated in an ambiguous manner, with each other in such a way that the resultant points of intersection lie within the expectancy range of the tooth topography previously determined on the basis of the first stripe patterns $M1_1$–$M1_4$. These points of intersection, which in their totality produce a definitive, clear topographic image of the tooth surface, are output by the computer 1 by way of the signal line 14, for example to an NC milling machine for the production of, for example, a copy of the measured tooth.

For the purpose of producing the patterns, instead of the LCD unit, stripe grids, mechanically displaceable interferometric laser apparatuses with adjustable deflection mirrors and other known apparatuses can also be used.

In order to take several partial views of the object to be measured which can be put together to give an overall view, it is advantageous to use a measuring probe which instead of one camera and one projector contains several projectors and cameras associated with each other in pairs.

What is claimed is:

1. A method for optically measuring objects, comprising the steps of:
   a) imaging at least one optical pattern on an object, said optical pattern having at least two brightness ranges, being produced by a light beam generated by at least one projector and diverging outward from a projector central point, and being arranged in a plane of projection of the projector,
   b) imaging on a sensor surface of at least one camera, the pattern imaged on the object, said camera being located in a given position relative to the projector and being directed at the object at a parallax angle relative to the projector, said image on the sensor surface being produced by a beam path converging toward a camera central point, said sensor surface including sensor elements representing camera side image points, including the steps of
      1) measuring light intensities on the sensor elements, and
      2) storing in a computer data values representing the measured light intensities;
   c) using the computer to determine a phase position of each camera-side image point from the measured light intensity on the sensor element representing the camera-side image point, and storing the determined phase positions in the computer, wherein the phase position of each camera-side image point corresponds to a phase position of an associated respective object side image point imaged on the object and is dependent on the vertical position of said associated object side image point;
   d) determining and storing in the computer the position in space, relative to a reference system of coordinates, of the projector central point, the camera central point, and the sensor elements of the sensor surface;
   e) splitting the pattern in the plane of projection of the projector into projector-side image points, and determining and storing in the computer the respective positions of the projector-side image points relative to the reference system of coordinates;
   f) using the computer to correlate camera-side image points and projector-side image points of equal phase position; and g) the computer determining the position in space, relative to the reference system of coordinates, of imaginary projector-side and camera-side straight lines passing through the correlated projector-side or camera-side image points of equal phase position and the projector central point or the camera central point respectively, on computer also determining points of intersection of the determined imaginary straight lines and the position of the respectively correlated object-side image points or object surface points.

2. Method according to claim 1, wherein as a pattern a stripe pattern is imaged on the object and in the plane of projection is split up into image point lines extending in the stripe direction, and the position in space of imaginary planes laid through the image point lines and the projector central point and also the space coordinates of the points of intersection of those of these planes and those camera-side straight lines which go through image point lines or camera-side image points of equal phase position respectively, are determined.

3. Method according to claim 1, wherein the pattern is imaged with analog brightness distribution on the object.

4. Method according to claim 3, wherein the pattern is imaged with sinusoidal brightness distribution on the object.

5. Method according to claim 1, wherein at least two stripe patterns, a first, rough stripe pattern with a comparatively small number of stripes and a second, fine stripe pattern with a comparatively large number of stripes, are imaged on the object one after the other and are evaluated, and in that the ambiguities, which are a result of the higher resolution (greater number of image points of equal phase position) of the second stripe pattern, in the correlation of the camera-side and projector-side image points or image point lines of equal phase position are eliminated by consideration of the camera-side and projector-side image points or image point lines of equal phase position of the first stripe pattern.

6. Method according to claim 1, wherein a stripe pattern is imaged on the object at least three times with, in each case, phase position shifted by the same phase angle transversely to the stripe direction, and is evaluated according to the known phase shift method for the exact determination of the phase position of the camera-side image points.

7. Apparatus for optically measuring objects, comprising:
a projector to generate a light beam diverging outward from a projector central point, to produce an optical pattern on an object to be measured, wherein the projector has, in a plane of projection, an LCD unit which can be activated by means of an LCD matrix for the purpose of producing different patterns and diverging light beams which radiate through the LCD unit for the purpose of imaging the patterns on the object to be measured, a camera for receiving an image of the pattern imaged on the object, wherein the camera is a CCD camera with a CCD unit, the CCD matrix of which splits up the pattern taken up into individual camera-side image points, a computer connected to the projector and to the camera to receive data and signals from, and to transmit data and signals to, the projector and the camera, wherein the computer delivers to the LCD unit for each projector-side image point a brightness signal which corresponds to the pattern to be produced, wherein the CCD camera delivers to the computer for each camera-side image point an evaluation signal which corresponds to the latter's measured brightness, and the computer effects the coordination of the image points of the LCD matrix and the CCD matrix and also the calculation of the space coordinates of the image points on the object side or the object surface points respectively.

* * * * *